United States Patent [19]

Müller

[11] Patent Number: 5,770,147
[45] Date of Patent: Jun. 23, 1998

[54] APPARATUS FOR THE IRRADIATION OF BODY FLUIDS BY ULTRAVIOLET LIGHT

[76] Inventor: Hans Müller, Reichenhaller Str. 49, 81547 München, Germany

[21] Appl. No.: 751,056

[22] Filed: Nov. 15, 1996

Related U.S. Application Data

[63] Continuation-in-part of PCT/EP96/02155 May 15, 1996.

[30] Foreign Application Priority Data

May 17, 1995 [DE] Germany .......................... 195 18 117.4
Aug. 29, 1995 [DE] Germany .......................... 195 31 751.3

[51] Int. Cl.⁶ ....................................................... A61L 2/00
[52] U.S. Cl. ........................... 422/24; 422/44; 250/432 R; 250/435; 250/437; 250/438; 204/133
[58] Field of Search ................... 422/24, 44; 250/432 R, 250/435, 437, 438; 204/193

[56] References Cited

U.S. PATENT DOCUMENTS 3,182,193   5/1965   Ellner et al. ............................ 250/43.5
3,894,236   7/1975   Hazelrigg ................................. 250/435

Primary Examiner—Stephen Walsh
Assistant Examiner—Eliane Lazar-Wesley
Attorney, Agent, or Firm—Klaus J. Bach

[57] ABSTRACT

In an apparatus for the irradiation of body fluids by ultraviolet light in a containment for receiving the body fluids which is disposed in the radiation range of an ultraviolet light source, the containment includes baffle means arranged so as to subject the body fluids circulated through the containment to turbulence whereby the body fluid in the containment is uniformly exposed to the UV radiation.

9 Claims, 2 Drawing Sheets

APPARATUS FOR THE IRRADIATION OF BODY FLUIDS BY ULTRAVIOLET LIGHT

This is a Continuation-In-Part application of International patent application PCT/EP96/02115 filed 15 May 1996 and claiming priority of the German application P 195 18 117.4/195 31 751.3 filed on 17 May 1995/29 Aug. 1995.

BACKGROUND OF THE INVENTION

The invention resides in an apparatus for the irradiation of body fluids, especially blood and/or tissue extracts, by ultraviolet light with a container in which the body fluids are disposed for the irradiation procedure.

Such apparatus are known for example from U.S. application Ser. No. 08/604,585 for use in therapeutical treatments in which for example blood is removed from a body, is enriched with oxygen and is then returned to the body through a quartz tube wherein it is exposed to ultraviolet radiation.

It is however desirable to subject the blood or body fluids to a full and uniform UV irradiation. This is not easily possible since the penetration depth of UV radiation into body fluids and particularly blood is relatively small. Furthermore, the body fluids have a relatively high viscosity so that, with the relatively low flow speeds through the quartz tube, a laminar flow pattern is established wherein the outer areas which are mainly exposed to the UV radiation remain on the outside and the inner flow areas remain in the inner tube part. As a result, laminar layers of body fluids pass through the quartz glass wherein the outer layer adjacent the wall of the quartz glass absorbs a substantial part of the UV radiation before the radiation can even reach the inner part of the laminar flow. This problem is particularly pronounced where the glass tube is irradiated only from one side since then only the areas of the glass tube adjacent the UV lamp are subjected effectively to the UV raidiation.

It is the object of the present invention to provide a simple apparatus for the irradiation of body fluids with ultraviolet light wherein the whole volume of the body fluid sample is uniformly exposed to the UV radiation and which can be utilized in various types of equipment in which body fluids need to be uniformly subjected to UV radiation.

SUMMARY OF THE INVENTION

With the apparatus according to the invention a body fluid sample taken from a patient and enclosed in, or flowing through, a container is subjected to sufficient turbulence so that, during the irradiation period, all parts of the fluid will uniformly come into contact with the inner wall of the container where the highest UV radiation intensity is present.

In one embodiment of the invention, the body fluid taken from a patient is conducted through a double tube cuvette with an inner and an outer tube so arranged that an annular space is formed through which the body fluid is conducted. Turbulence inducing baffle plates are arranged either on the inner side of the outer tube or on the outer side of the inner tube or on both. With this arrangement, the body fluid is conducted through the annular space in the cuvette in a relatively thin layer and is, at the same time, subjected to turbulence so that a uniform irradiation of all the fluid particles is achieved in the desired manner.

The advantages and various features of the present invention will be described below on the basis of the accompanying drawings.

DESCRIPTION OF THE PREFERRED EMBODIMENTS

Figure 1:
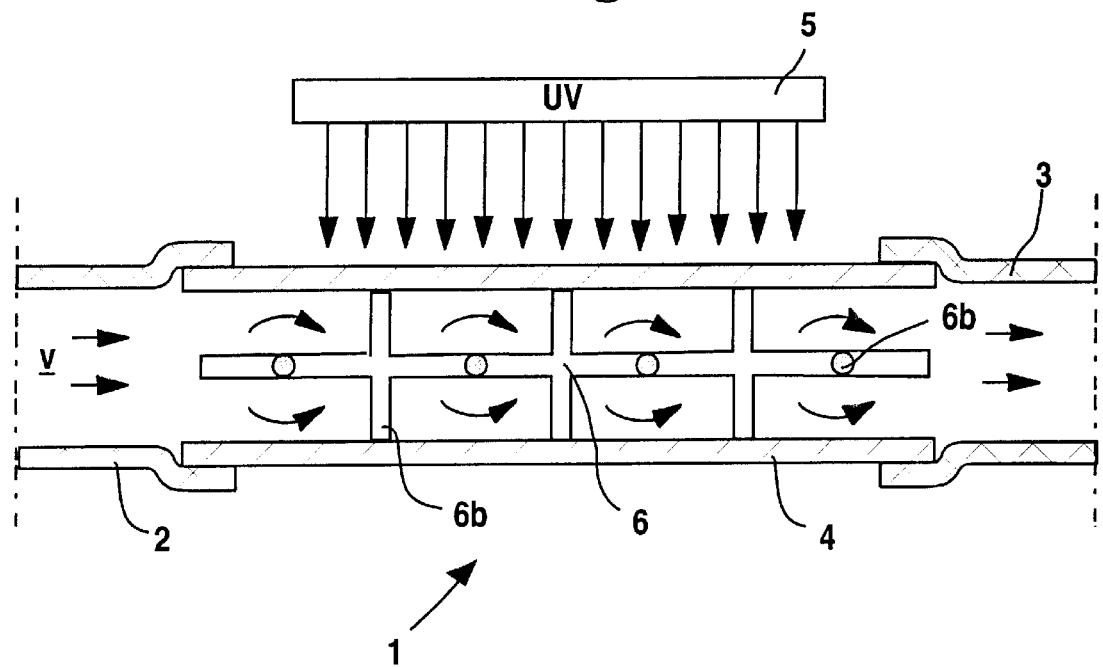
FIG. 1 is a longitudinal cross-sectional view of an irradiation apparatus according to the invention wherein a body fluid flows through a containment which is subjected to UV radiation and which includes a baffle structure providing for uniform turbulence in the body fluid flow.

FIG. 1 is a side view of a first embodiment of an irradiation apparatus 1 according to the invention to which a body fluid such as blood is admitted through a supply line 2 and conducted away through a discharge line 3. The apparatus includes a containment 4 through which the body fluid flows and which is subjected to ultraviolet radiation. The containment 4 consists of a UV radiation transparent quartz glass cuvette. In FIG. 1, the local flow vectors V of the fluid flow are indicated by arrows.

Because in medical therapeutical processes, the flow speeds must be relatively low, typically not more than a few centimeters per minute, only a laminar flow would be obtained in the glass cuvette at the relatively high viscosity of the body fluids. In a tube such a laminar flow has a parabolic flow profile wherein hollow cylindrical fluid layers are formed which slide along one another but which have no radial flow components so that no mixing takes place.

In an arrangement like the one shown in FIG. 1, but without the baffle structure, only one outer blood layer would be exposed to the UV radiation of an adjacent UV lamp 5 and only the part of the layer flowing on the side of the lamp 5 would be subjected to UV radiation. The blood flowing on the opposite side or in the center of the cuvette would receive little or no exposure because the blood is highly UV light absorbent so that the UV light penetration is very shallow.

To avoid this, the containment 4 according to the present invention includes a baffle structure 6. The baffle structure 6 may be provided for example in the form of a turbulence inducing rod structure as shown in a perspective view in FIG. 3. This baffle structure includes a longitudinal rod 6a extending along the axis of the cuvette 4 and a plurality of transverse bars 6b wherein subsequent transverse bars 6b are turned about the cuvette axis by 90° C. with respect to one another. The transverse bars 6b prevent a laminar flow in the interior of cuvette as they generate local flow vectors v with flow components in radial direction whereby turbulence is generated in the fluid flow through the cuvette.

Figure 2:
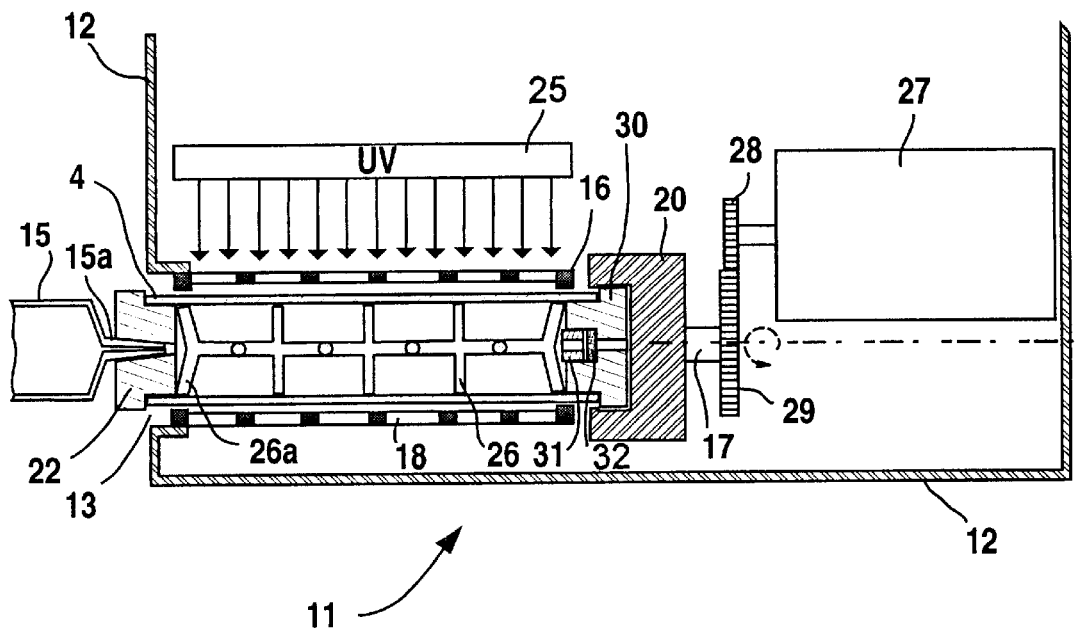
FIG. 2 is a longitudinal cross-sectional view of a particular embodiment of the invention wherein the containment receiving the body fluid is rotatably supported adjacent a UW lamp and includes a baffle structure providing for uniform turbulence in the body fluid flow.

FIG. 2 shows another embodiment of the invention wherein an irradiation apparatus 11 includes a housing 12 with an opening 13 for inserting a containment of cuvette 4. The opening 13 leads to the interior of a guide tube 16 which is arranged coaxially with a drive shaft 17 and which is mounted to the housing 12 for example adjacent the opening 13.

The guide tube 16 consists of a material which is transparent to the radiation generated by a UV lamp 25 disposed in the housing 12 or it has slots 18 for the passage of ultraviolet light as shown in FIG. 2.

In the area of the guide tube opposite the opening 13, the housing 12 includes an adapter 20 which is supported on the drive shaft 17 which is rotated by a drive motor 17 via a motion transmission comprising two gears 28, 29. The front end of the cuvette 4, in the direction of insertion into the guide tube 16, includes means for engagement with the adapter 20 so that the cuvette 4 can be rotated by the motor 27.

A cuvette can be filled with blood taken from a patient by way of an injector 15 which has a conical end 15a which is placed into a bore centrally extending through a cuvette plug 22. A second plug 30 is disposed at the opposite end of the cuvette which includes a second central bore. A bacteria filter 32 is disposed in this second bore and is secured therein by means of an auxiliary plug 31 which also includes a bore. When body fluid is filled into the cuvette 4, air can be expelled through the bore and the bacteria filter in the second plug.

The cuvette, filled with body fluid, and including the injector attached thereto is inserted through the opening 13 of the housing 12 into the irradiation apparatus until its front end is engaged with the adapter 20. When the adapter 20 is rotated by the drive motor 27, the cuvette is rotated together with the adapter so that the cuvette is exposed to the UV radiation of the UV lamp 25 over the whole circumference in a uniform way and the fluid in the cuvette is moved circularly with the cuvette 4.

The flow baffles 26 provide additionally for turbulence so that radial flow components are generated which carry fluid outwardly to the inner surfaces of the cuvette whereby a highly uniform irradiation of the fluid volume in the cuvette is achieved.

After termination of the irradiation procedure, the cuvette 4 is disengaged from the adapter 20 and is removed from the housing 12. Then the irradiated content of the cuvette can be sucked out by way of the injector 15 and can be returned to the patient. The bacteria filter 32 prevents contamination of the cuvette content when air is sucked into the cuvette being emptied.

Figure 3:
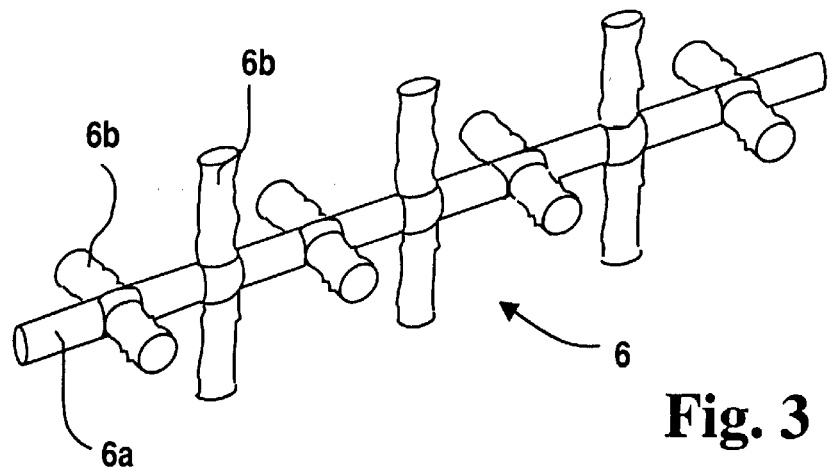
FIGS. 3 and 4 show different embodiments for baffle structures to be disposed in a body fluid containment and, FIG. 5 shows a double tube cuvette for use as a body fluid containment.

The baffle structure as shown in FIG. 3 has the advantage that it can be made in a cost effective manner since it consists of plastic and can be made efficiently by injection molding. It can be used as a throw-away part which can be disposed after irradiation of a body fluid sample together with the glass cuvette.

Basically, however, baffle structures other than that shown in FIG. 3 can be used in the cuvette 4 as long as they provide for sufficient turbulence within the cuvette.

If a baffle structure is used in a cuvette as shown in FIG. 2, wherein both ends are closed by plugs 22 and 30, it is advantageous if the baffle structure includes at opposite ends of the axial rod an outwardly inclined rib structure 26a which serves to hold the central longitudinal rod of the baffle structure at a certain distance from the bores in the plugs 22 and 30 so that these bores are not blocked and the cuvette can always be easily filled and emptied.

Figure 4:
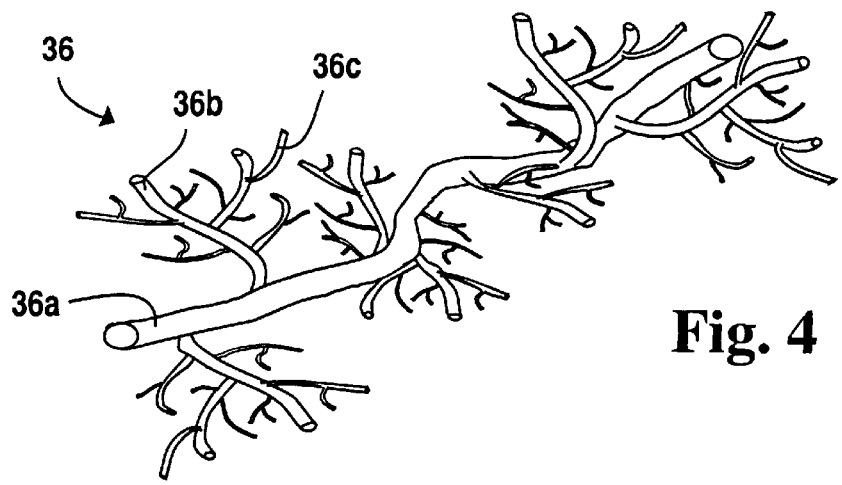

Instead of having a shape as indicated in FIGS. 1–3, the baffle structure may have a coral tree-like shape as shown in FIG. 4 and indicated by numeral 36. This baffle structure includes a central trunk 36a extending along the axis of the cuvette and a plurality of irregularly arranged branches 36b with fine irregularly arranged threads 36c. The fine threads 36c prevent a laminar fluid flow within the cuvette in a particularly effective way since any laminar flow is repeatedly disturbed whereby turbulence is effectively generated in the fluid flow.

With the arrangement according to the invention, turbulence in the fluid flow in the cuvette can be generated in an efficient manner when compared to other means such as magnetic stirring means as they are used in chemistry laboratories for the mixing of fluids and the rapid dissolution of salts in solvents for which a rotating magnetic field is required to actuate magnetic stirring rods. The arrangement according to the invention does not require outer drive means such as a rotating magnetic field.

Figure 5:
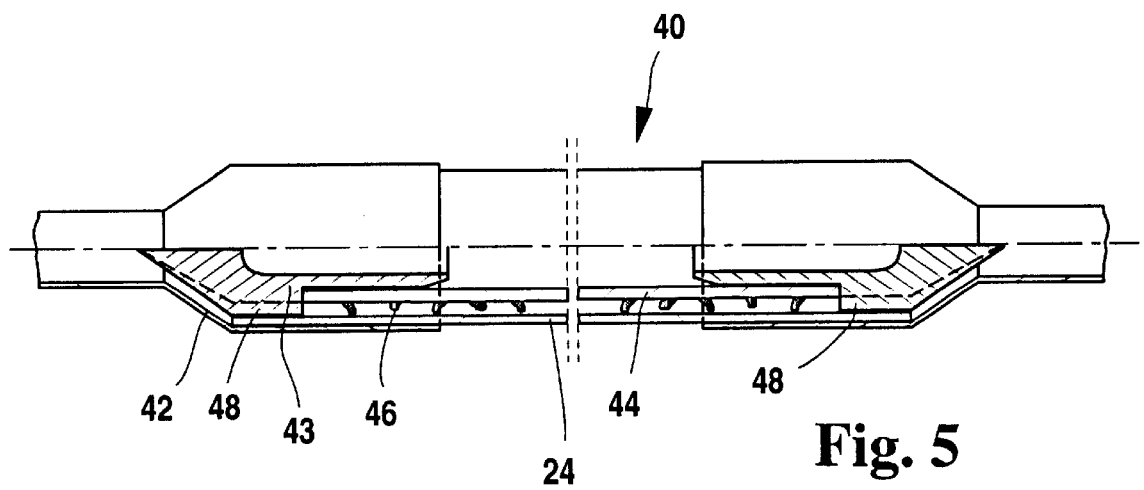

FIG. 5 shows another embodiment of the invention with a double tube cuvette 40 having an inner tube 44 whose opposite ends are closed by plugs 43. This arrangement is disposed in an outer tube 24 onto which hose connections 42 are placed at opposite ends for the supply of body fluids to, and their removal from, the double tube cuvette. The outer surface of the inner tube 44 is provided with baffles 46 of any shape that will induce turbulence to the body fluid conducted through the annular space between the inner and outer tubes. In order to provide for passages for the body fluid, the plugs 43 are provided with ribs 48 which also center the plugs and the inner tube 44 within the outer tube 24.

With this arrangement, body fluids passing through the annular space between the inner and outer tubes are subjected to sufficient turbulence and if the baffles are appropriately shaped, also to a circumferential flow pattern so that uniform irradiation of the body fluids is achieved.

Means may be provided similar to those shown in FIG. 2, whereby the hose connections 42 may be engaged for rotating the double tube cuvette during exposure to UV radiation. For this purpose, a gear drive may be provided which rotates the double tube cuvette essentially as shown in FIG. 2.

What is claimed is:

1. An apparatus for the irradiation of body fluids by ultraviolet light, particularly of blood and other tissue extracts, said apparatus comprising a removable tubular containment for receiving the body fluids and an ultraviolet light source having a radiation range in which said containment can be placed, said containment including baffle means arranged so as to subject body fluids circulated therethrough to turbulence, said baffle means having a multitude of integral baffle structures including a longitudinal rod extending axially in said containment and transverse bars branching off said longitudinal rod, past which said body fluids flow and which convert laminar flow to a turbulent flow such that the body fluid in said containment is uniformly exposed to the UV radiation emitted by said light source.

2. An apparatus for the irradiation of body fluids by ultraviolet light according to claim 1, wherein said containment is a glass tube, said longitudinal rod extends along the axis of said glass tube and said transverse bars are radial rods extending from said longitudinal rod toward said glass tube.

3. An apparatus for the irradiation of body fluids by ultraviolet light according to claim 2, wherein said longitudinal rod is provided at its opposite axial ends with axially outwardly inclined fins which engage plug structures mounted in the ends of said glass tube and retain said longitudinal rod axially centered within said glass tube.

4. An apparatus for the irradiation of body fluids by ultraviolet light according to claim 1, wherein said containment comprises two concentrically arranged glass tubes of different diameters so as to form an annular flow passage between the two glass tubes which provides a predetermined flow path width for said body fluid through said annular space and wherein said baffle means are provided on at least one of the outer surface of said inner tube and the inner surface of said outer tube.

5. An apparatus for the irradiation of body fluids by ultraviolet light according to claim 4, wherein said double tube containment is rotatably supported in the radiation range of said UV light source.

6. An apparatus for the irradiation of body fluids by ultraviolet light according to claim 1, wherein said containment is rotatably supported in the radiation range of said UV light source.

7. A tubular containment or receiving body fluids, said tubular containment having an outer wall and including baffle means arranged so as to subject body fluids circulated through that containment to turbulence, said baffle means extending axially in said containment and having transverse branches which extend up to said outer wall and which convert a laminar flow of body fluids conducted through said tubular containment to a turbulent flow.

8. A tubular containment according to claim 7, wherein said tubular containment is a glass tube and said baffle neans longitudinal rod is provided at its opposite axial ends with axially outwardly inclined radical fins which engage end walls of said glass tube and retain said baffle means centered within said glass tube.

9. A tubular containment comprising two concentrically arranged glass tubes of different diameters so as to form an annular flow passage between the two glass tubes which provides a predetermined flow path width for body fluids conducted through said containment, and baffles provided on at least one of either the outer surface of said inner glass tube so as to extend to the inner surface of the outer glass tube or the inner surface of said outer glass tube so as to extend toward the outer surface of said inner glass tube.

* * * * *